United States Patent
Elgort et al.

(10) Patent No.: US 8,765,099 B2
(45) Date of Patent: Jul. 1, 2014

(54) MAGNETIC RESONANCE IMAGING HYPERPOLARIZATION OF LIQUIDS OR SOLIDS BY LIGHT WITH ORBITAL ANGULAR MOMENTUM

(75) Inventors: Daniel R. Elgort, New York, NY (US); Lucian Remus Albu, Forest Hills, NY (US)

(73) Assignee: Koninklijke Philips N.V., Eindhoven (NL)

( * ) Notice: Subject to any disclaimer, the term of this patent is extended or adjusted under 35 U.S.C. 154(b) by 785 days.

(21) Appl. No.: 12/808,385

(22) PCT Filed: Dec. 19, 2008

(86) PCT No.: PCT/IB2008/055444
§ 371 (c)(1),
(2), (4) Date: Jun. 16, 2010

(87) PCT Pub. No.: WO2009/081360
PCT Pub. Date: Jul. 2, 2009

(65) Prior Publication Data
US 2010/0317959 A1 Dec. 16, 2010

Related U.S. Application Data

(60) Provisional application No. 61/015,210, filed on Dec. 20, 2007.

(51) Int. Cl.
*A61B 5/055* (2006.01)

(52) U.S. Cl.
USPC ............................. 424/9.3; 424/9.37; 600/410

(58) Field of Classification Search
USPC ............ 600/407–436, 473–480; 424/9.3, 9.4, 424/9.37
See application file for complete search history.

(56) References Cited

U.S. PATENT DOCUMENTS

| | | | |
|---|---|---|---|
| 4,525,672 A | | 6/1985 | Lam et al. |
| 4,586,511 A | * | 5/1986 | Clark, Jr. ..................... 424/9.37 |
| 4,613,818 A | * | 9/1986 | Battocletti et al. ............ 324/306 |
| 5,357,959 A | * | 10/1994 | Fishman ....................... 600/420 |

(Continued)

OTHER PUBLICATIONS

Physical Background: Angular Momentum, Optical Pumping; downloaded on Nov. 13, 2007 http://fuj.physik.uni-dortmund.de/-suter/lamr/background.html.

(Continued)

*Primary Examiner* — Sanjay Cattungal

(57) ABSTRACT

In magnetic resonance imaging (MRI), selected magnetic dipoles in a subject are aligned with a main magnetic field for later manipulation, and signals received after such manipulations are used to create image representations of the subject. One drawback is that even powerful magnetic fields can only align a very small percentage of dipoles in the region of the field. Electromagnetic radiation endowed with orbital angular momentum (OAM) aligns dipoles along the direction of travel of the radiation, but at a much higher percentage; as high as 100% of the dipoles in the region can be aligned. Resultantly, resonance signals emanating from the region are several orders of magnitude stronger than signals emanated using traditional MRI techniques. All electromagnetic radiation, including visible light can be endowed with OAM and used to hyperpolarize a region of interest.

20 Claims, 5 Drawing Sheets

(56) References Cited

U.S. PATENT DOCUMENTS

| | | | |
|---|---|---|---|
| 5,545,396 A * | 8/1996 | Albert et al. | 424/9.3 |
| 5,642,625 A * | 7/1997 | Cates et al. | 62/55.5 |
| 5,785,953 A * | 7/1998 | Albert et al. | 424/9.3 |
| 6,051,208 A * | 4/2000 | Johnson et al. | 424/9.3 |
| 6,278,893 B1 * | 8/2001 | Ardenkj.ae butted.r-Larson et al. | 600/420 |
| 6,426,058 B1 * | 7/2002 | Pines et al. | 424/9.3 |
| 6,453,188 B1 * | 9/2002 | Ardenkjaer-Larsen et al. | 600/420 |
| 6,818,202 B2 * | 11/2004 | Pines et al. | 424/9.3 |
| 7,282,911 B2 | 10/2007 | Xiang et al. | |
| 7,295,006 B2 * | 11/2007 | Potapov et al. | 324/306 |
| 7,576,538 B2 * | 8/2009 | Meersmann et al. | 324/309 |
| 2004/0005273 A1 * | 1/2004 | Driehuys et al. | 424/9.3 |

OTHER PUBLICATIONS

Bingelyte, V., et al.; Optically controlled Three-dimensional rotation of microscopic objects; 2003; Applied Physics Letters; 82(5)829-831.

Bouchal, Z., et al.; Selective excitation of vortex fibre modes using a spatial light modulator; 2005; New Journal of Physics; 7:125.

Elgort, D. R., et al.; Direct Optical Hyperpolarization of Liquids; 2008; Proc. Intl. Soc. MRM; p. 3200.

Leach, J., et al.; Observation of chromatic effects near a white-light vortex; 2003; New Journal of Physics; 5(1)154.

Miyamoto, Y., et al.; Detection of orbital angular momentum superposition photon states using hologram and path interferometer; 2007; IEEE Trans on Lasers and Electro-Optics;p. 1.

Zadernovsky, A. A.; Excitation of Nuclei by Photon Beams Carrying Orbital Angular Momentum; 2006; Laser Physics; 16(4)571-575.

* cited by examiner

MAGNETIC RESONANCE IMAGING HYPERPOLARIZATION OF LIQUIDS OR SOLIDS BY LIGHT WITH ORBITAL ANGULAR MOMENTUM

CROSS REFERENCE TO RELATED APPLICATIONS

This application claims the benefit of U.S. provisional application Ser. No. 61/015,210 filed Dec. 20, 2007, which is incorporated herein by reference.

FIELD OF THE INVENTION

The present application relates to the diagnostic imaging arts. It finds particular application in magnetic resonance imaging of regions near the surface of a subject's skin or accessible with a probe or catheter, and will be described with particular reference thereto. It is to be appreciated, however, that it is also applicable to other regions or areas, contrast enhanced imaging, spectroscopy and is not limited to the aforementioned applications.

BACKGROUND OF THE INVENTION

Conventional magnetic resonance imaging (MRI) uses powerful magnetic fields to align, that is, polarize the spin vector of protons, particularly protons inside the hydrogen nuclei in water molecules. Using RF excitation pulses, the system knocks the spin vectors out of alignment, and as they re-align, they produce a resonance signal that is used for imaging. This approach, however, only enables MRI scanners to polarize a small fraction of the water protons; for example, a 1.5 Tesla magnetic field, at room temperature, will polarize only about 3 protons out of one million. This inefficiency places limitations on the resolution, sensitivity, and dynamic contrast range of MRI. MRI finds extensive application, in part due to its sensitivity to the chemical characteristics of tissue components, in the characterization and differentiation of soft tissues. Other applications include fluid chemical analysis of small molecules and biomolecules (e.g. protein-ligand interactions, protein folding, protein structure validation, and protein structure determination), solid state analysis (structural), dynamics of time-variable systems, and the like.

Conventional MRI is characterized in that in sets up a highly uniform static main magnetic field (also called the $B_0$ magnetic field), creating nuclear spin precession at a corresponding narrow band of resonance frequencies. A drawback is that the typical setup requires large magnets, gradient field coils, and radio frequency (RF) coils, adding to the bulk, complexity, and cost of the system.

Micro MRI systems exist that overcome some of these drawbacks. In one example, permanent magnets on the tip of a catheter generate a static magnetic field at the catheter tip. A micro MRI system also has a high quality receiving coil built into the tip, such as a Helmholtz micro coil. This allows for local imaging of blood vessels without the need for external magnets or coils. Gradient coils facilitate Fourier images or point-by-point imaging/analysis to be performed without gradient coils. Some advantages are low cost, patient accessibility, compatibility with existing tools, and high resolution. Drawbacks include the aforementioned problem of a small imaging region and only polarizing a few protons per million, but this is in part balanced by the proximity to the resonating protons.

Spin-exchange optical pumping techniques, using circularly polarized light, are able to increase noble gas dipole polarization to close to 100% that is, hyperpolarize these gases in a limited region. These methods, however, have only been shown to be suitable for hyperpolarizing low density noble gases, such as Xenon or Helium, under controlled laboratory conditions. Such techniques have been used for applications like contrast enhanced MRI of the pulmonary airways; a subject inhales the prepared gas (breathing air in which some of the nitrogen has been replaced with hyperpolarized Xenon), and then MR data are collected. Existing methods have not contemplated hyperpolarization of liquids or solids which would enable the standard MR imaging signal associated with blood and biological tissue to be enhanced.

The present application provides a new and improved optical polarization device which overcomes the above-referenced problems and others.

SUMMARY OF THE INVENTION

In accordance with one aspect, a light-based hyperpolarization device is provided. A light source emits light. A phase hologram imparts orbital angular momentum to the light. A spatial filter filters out a portion of the light and allows a portion of the light with a pre-determined amount of orbital angular momentum to pass. At least one optical element directs the light that passes the spatial filter to a region of interest to be hyperpolarized.

In accordance with another aspect, a magnetic resonance system is provided, including a light-based hyperpolarization device that polarizes a selected dipole via transferred orbital angular momentum. An RF system induces resonance in the polarized dipoles and receives resonance signals.

In accordance with another aspect, a surface probe is provided. A light output unit directs light to penetrate tissue of a patient. A light-based hyperpolarization system imparts orbital angular momentum to generated light. The light to which orbital angular momentum has been imparted is discharged through the light output unit to polarize selected dipoles in the patient.

In accordance with another aspect, a catheter is provided. An elongated portion terminates in a working end configured to be inserted in a patient. A light-based hyperpolarization system imparts orbital angular momentum to generated light. The light to which orbital angular momentum has been imparted is discharged through the light output unit to polarize selected dipoles in the patient.

In accordance with another aspect, a method of resonance imaging is provided. A selected dipole is polarized via transferred orbital angular momentum. Resonance is induced in the polarized dipoles. Resonance signals are received.

One advantage is that blood can be more effectively imaged using nuclear resonance without aid of chemical contrast agents.

Another advantage lies in improved access to the subject.

Another advantage resides in lower cost.

Another advantage lies in improved resonance signal strengths.

Another advantage lies in improved resolution.

Another advantage of some embodiments is the elimination of large magnetic fields and the associated hardware for generating them, etc.

Still further advantages of the present invention will be appreciated by those of ordinary skill in the art upon reading and understand the following detailed description.

BRIEF DESCRIPTION OF THE DRAWINGS

These and other aspects will be described in detail hereinafter, by way of example, on the basis of the following embodiments, with reference to the accompanying drawings, wherein.

Corresponding reference numerals when used in the various figures represent corresponding elements in the figures.

DETAILED DESCRIPTION OF EMBODIMENTS

Orbital angular momentum (OAM) is an intrinsic property of all azimuthal phase-bearing light, independent of the choice of axis about which the OAM is defined. When interacting with an electronically distinct and isolated system, such as a free atom or molecule, OAM can be transferred from the light to the matter.

Various experiments have used the interaction of OAM-endowed light with matter, for example, optical tweezers, high-throughput optical communication channels, optical encryption techniques, optical cooling (Bose-Einstein condensates), entanglement of photons with OAM, and entanglement of molecule quantum numbers with interacting photons' OAM. Because angular momentum is a conserved quantity, the OAM of absorbed photons is transferred in whole to interacting molecules. As a result, affected electron states reach saturated spin states, angular momentum of the molecule about its own center of mass is increased and oriented along the propagation axis of the incident light, and magnetons precession movement of the molecules are also oriented along the propagation axis of the incident light. These effects make it possible to hyperpolarize nuclei within fluids by illuminating them with light-carrying spin and OAM.

An analysis of electromagnetic fields shows that there is a flow of electromagnetic energy with one component that travels along the vector of the beam propagation, and a second component that rotates about the axis of the beam propagation. The second component is proportional to the angular change of the potential vector around the beam propagation. This is significant because the rotational energy flow is proportional to l, the OAM value, and the rotational energy transferred to molecules with which the light interacts is increased with the value of the OAM.

Light-carrying spin and OAM is absorbed by molecules. Since angular momentum is a conserved quantity, the total angular momentum of the system (both the radiation and the matter) is not changed during absorption and emission of radiation. When a photon is absorbed by an atom, its angular momentum is transferred to the atom. The resulting angular momentum of the atom is then equal to the vector sum of its initial angular momentum plus the angular momentum of the absorbed photon.

Figure 1:
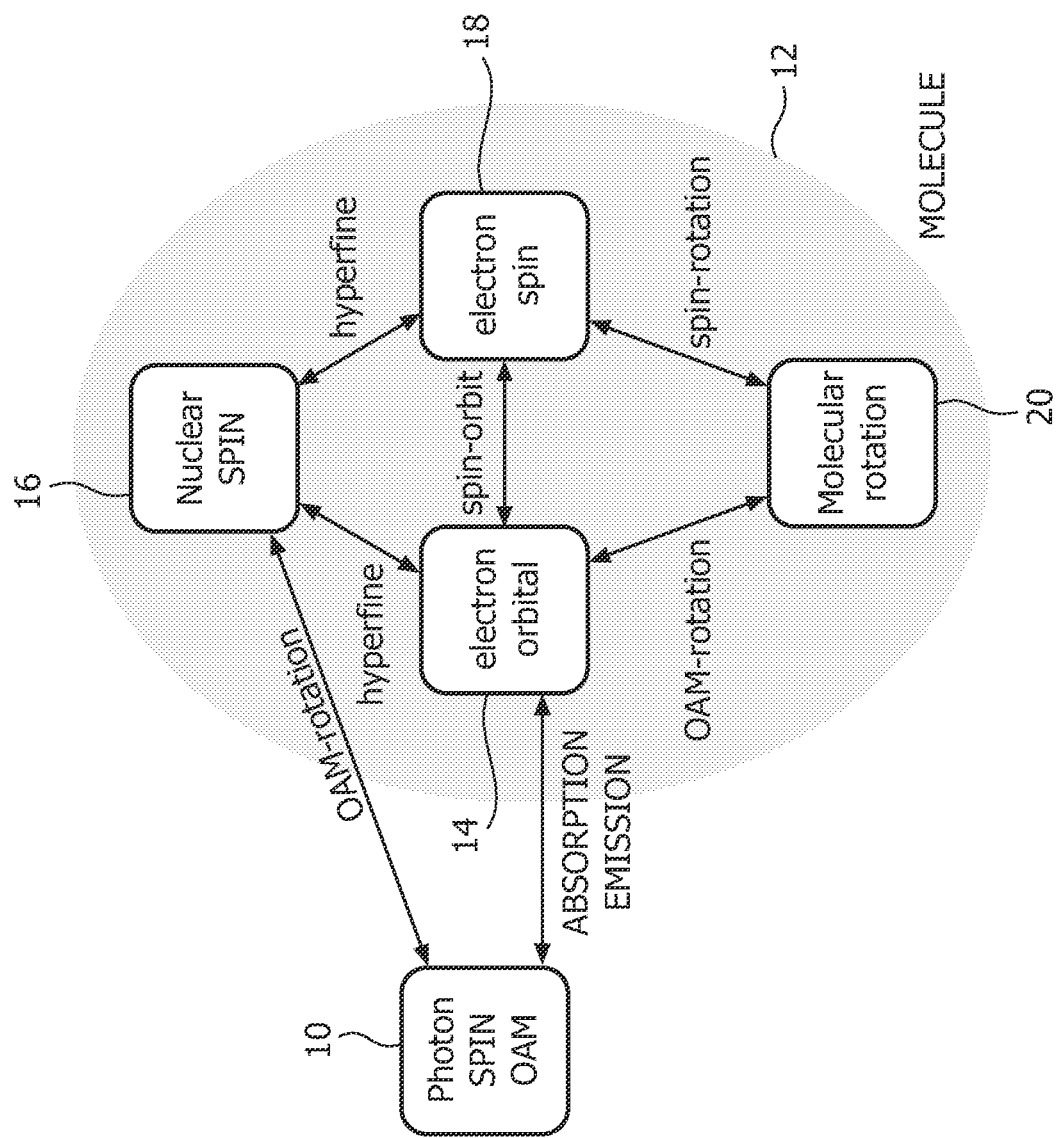
FIG. 1 is a diagrammatic illustration of a molecule interacting with an incident photon.

With reference to FIG. 1, when a photon 10 interacts with a molecule 12, only the OAM of the electrons 14 is directly coupled to the optical transitions. The different types of angular momentum, however, are coupled to each other by various interactions that allow the polarization to flow from the photon 10 through the electron orbital 14 to nuclear spin 16, electron spin 18 and molecular rotation 20 reservoirs, as shown in FIG. 1. The magnitude of the interaction between the photon 10 and the molecule 12 is proportional to the OAM of the photon 10. Resultantly, the molecular rotation value and orientation changes to align along the direction of propagation of the light, and align molecular nuclei along the same direction. The momenta of molecules are changed in that they are aligned in a direction along the propagation axis of the incident light by light endowed with spin and OAM proportional to the OAM content of the light. In some embodiments, the Applicant supplements or replaces the function of the $B_0$ field in conventional MRI by electromagnetic radiation endowed with OAM, as described above.

Figure 2:
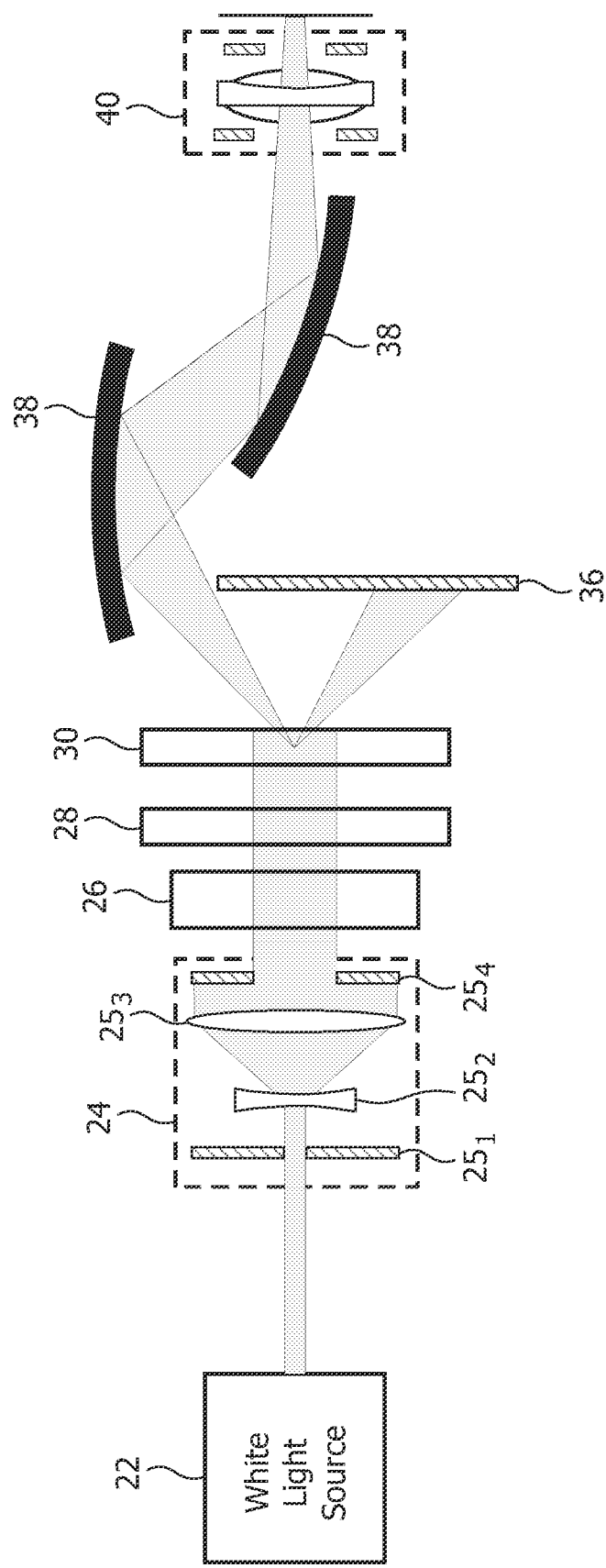
FIG. 2 is an optical diagram of a device for generating polarized light beams endowed with orbital angular momentum, in accordance with the present application.

With reference now to FIG. 2, an exemplary arrangement of optical elements is shown for endowing light with OAM. It is to be understood that any electromagnetic radiation can be endowed with OAM, not necessarily only visible light. The described embodiment uses visible light, which interacts with the molecules of interest, and has no damaging effect on living tissue. Light/radiation above or below the visible spectrum, however, is also contemplated. A white light source 22 produces visible white light that is sent to a beam expander 24. In alternate embodiments, the frequency and coherence of the light source can be used to manipulate the signal if chosen carefully, but such precision is not essential. The beam expander includes an entrance collimator $25_1$ for collimating the emitted light into a narrow beam, a concave or dispersing lens $25_2$, a refocusing lens $25_3$, and an exit collimator $25_4$ through which the least dispersed frequencies of light are emitted. In one embodiment, the exit collimator $25_4$ narrows the beam to a 1 mm beam.

After the beam expander 24, the light beam is circularly polarized by a linear polarizer 26 followed by a quarter wave plate 28. The linear polarizer 26 takes unpolarized light and gives it a single linear polarization. The quarter wave plate 28 shifts the phase of the linearly polarized light by ¼ wavelength, circularly polarizing it. Using circularly polarized light is not essential, but it has the added advantage of polarizing electrons.

Figure 3:
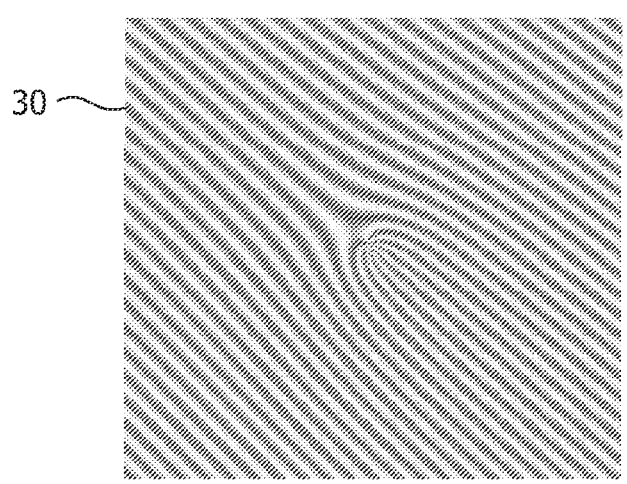
FIG. 3 is an enlarged view of a computer generated phase hologram for endowing incident light with orbital angular momentum, in accordance with the present application.

Next, the circularly polarized light is passed through a phase hologram 30. An example of a phase hologram 30 is depicted in FIG. 3. The phase hologram 30 imparts OAM and spin to an incident beam. The value "l" of the OAM is a parameter dependent on the phase hologram 30. In one embodiment, an OAM value l=40 is imparted to the incident light, although higher values of l are theoretically possible. The phase hologram 30 is a computer generated element and is physically embodied in a spatial light modulator, such as a liquid crystal on silicon (LCoS) panel, 1280×720 pixels, 20×20 $\mu m^2$, with a 1 µm cell gap. Alternately, the phase hologram 30 could be embodied in other optics, such as combinations of cylindrical lenses or wave plates. The spatial light modulator has the added advantage of being changeable, even during a scan, with a simple command to the LCoS panel.

Figure 4:
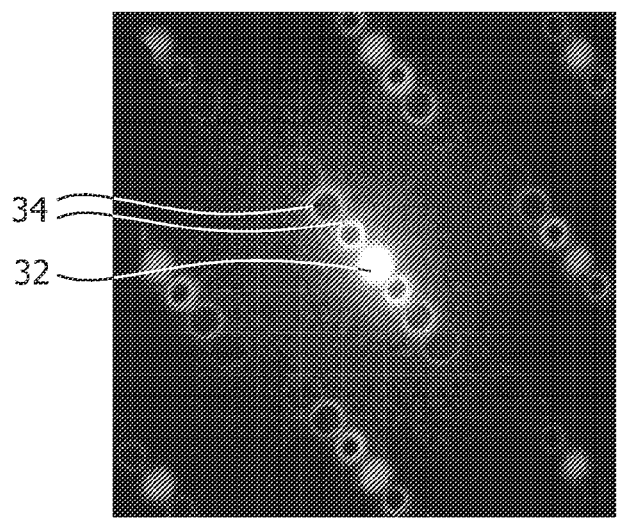
FIG. 4 is a diffraction projection of a light beam after it passes through the phase hologram of FIG. 3.

Not all of the light that passes through the holographic plate 30 is imparted with OAM and spin. With reference now to FIG. 4, a projection of the light that passes through the holographic plate 30 is depicted. Generally, when electromagnetic waves with the same phase pass through an aperture, it is diffracted into a pattern of concentric circles some distance away from the aperture (Airy pattern). The bright spot (Airy disk) 32 in the middle represents the $0^{th}$ order diffraction, in this case, that is light with no OAM. The circles 34 adjacent the bright spot 32 represent diffracted beams of different harmonics that carry OAM. This distribution results because the probability of OAM interaction with molecules falls to zero at points far from the center of the light beam or in the center of the light beam. The greatest chance for interaction occurs on a radius corresponding to the maximum field distribution, that is, for circles close to the Airy disk. Therefore, the maximum probability of OAM interaction is obtained with a light beam with a radius as close as possible to the Airy disk radius.

Figure 5:
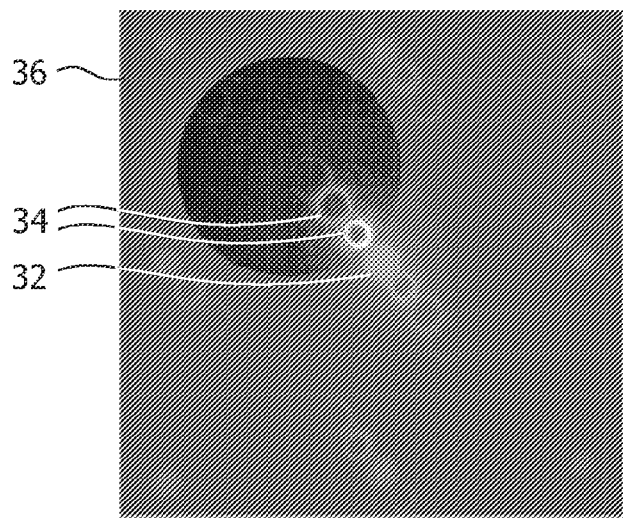
FIG. 5 depicts a spatial filter overlaid on the diffraction projection of FIG. 4.

With reference again to FIG. 2, a spatial filter 36 is placed after the holographic plate to selectively pass only light with OAM and spin. An example of such a filter is shown in FIG. 5. The $0^{th}$ order spot 32 always appears in a predictable spot, and thus can be blocked. As shown, the filter 36 allows light with OAM to pass. Note that the filter 36 also blocks the circles that occur below and to the right of the bright spot 32. Since OAM of the system is conserved, this light has OAM that is equal and opposite to the OAM of the light that the filter 36 allows to pass. It would be counterproductive to let all of the light pass, because the net OAM transferred to the target molecule would be zero. Thus, the filter 36 only allows light having OAM of one polarity to pass.

With continuing reference to FIG. 2, the diffracted beams carrying OAM are collected using concave mirrors 38 and focused to the region of interest with a fast microscope objective lens 40. The mirrors 38 may not be necessary if coherent light were being used. A faster lens (having a high f-number) is desirable to satisfy the condition of a beam waist as close as possible to the size of the Airy disk. In alternate embodiments, the lens 40 may be replaced or supplemented with an alternative light guide or fiber optics.

In one embodiment, the polarized light is used to supplement the $B_0$ field of an existing scanner. In this embodiment, the light is emitted parallel to the $B_0$ field, so that the effects complement each other, that is, the nuclei are aligned in the same direction due to both the $B_0$ field and the polarized light. Traditional spatial encoding and RF excitation can be used, but with the optical alignment, the resonance signal can be seven to eight orders of magnitude stronger, leading to increased signal to noise ratio, better signal strength, and improved resolution, on the order of micrometers. Alternatively, the polarized light beam is applied along a direction other than parallel to the $B_0$ field, to produce concurrent dipoles with different relaxation orientations.

In another embodiment, the typical $B_0$ field is replaced entirely by optical perturbation. In such an embodiment, the large, complex main magnet is eliminated, greatly freeing up space and making the subject more accessible. Of course, in such an embodiment, resonance signals would only be received from dipoles accessible by the optical delivery system. Spatial encoding is achieved, for example, by gradient magnetic fields produced by weaker, homogeneous magnets. Alternatively, spatial encoding is achieved optically. Polarized light along one axis serves to align the dipoles along a single direction, while an array of light generators along another axis perform the spatial encoding. The light is used to spatially encode the resonance by phase encoding and frequency encoding. Frequency encoding is provided by magnets or by light.

One application of using the OAM-endowed light is the imaging of blood vessels. The light emitting system previously described may be embodied in a needle or catheter 68 in FIG. 6 and inserted directly into the bloodstream. In the illustrated embodiment, the light source 22 is conveniently located outside of the intravenous device and fiber optics is used to channel the light thereto. The catheter 68 is then inserted into the subject, such as through the femoral artery, and advanced to the region or anatomy of interest. The light aligns dipoles in illuminated vessel walls or other adjacent tissues analogous to a conventional $B_0$ field. The aligned dipoles are caused to resonate by the application of RF signals by an RF coil in the tip of the catheter 68 or by external RF coils. The induced resonance signals are received by the RF coils in the tip of the catheter for a high signal-to-noise ratio. External RF receive coils, e.g. surface coils are also contemplated.

The resonance can be spatially encoded in various ways. In one embodiment, the resonance is excited in and detected from a single voxel at a time. In another embodiment, external or at-the-tip gradient magnetic field coils phase- and frequency-encode the resonance. In another embodiment, a permanent magnet or magnetic field coil adjacent the tip encodes frequency and the OAM enhanced light is used for phase encoding. Optionally, a very low field magnet provides a weak $B_0$ field aligned with the OAM-endowed induced polarization. The $B_0$ field determines the resonance frequency. The higher the $B_0$ field, the higher the resonance frequency. High $B_0$ fields, however, generally have high associated magnet costs and larger magnets that inhibit patient access.

In another embodiment, blood passing by the light emitter at the tip of the catheter 68 or a surface probe 66 is aligned, particularly hyperpolarized, and it can be imaged as it flows to a downstream portion of the body. For instance, if the light source illuminates blood flowing through the carotid artery, the hyperpolarized blood exhibits high signal strengths in the blood vessels in the brain. Because the carotid artery passes close to the surface, it can be illuminated from the surface without using an invasive procedure such as a catheter. In this embodiment, the polarized light can be used in lieu of, or to supplement traditional chemical contrast in a conventional MRI system. Using polarized light is not as time-sensitive as some chemical contrast agents, as the transit time to the patient and ultimately to the region of interest would not be critical. Also, chemical contrast agents carry the disadvantage of being hard on the patient's kidneys and liver, and elimination of the use of such chemical contrast agents would therefore be beneficial.

Typically, magnetic resonance imaging is performed using certain dipoles that are more responsive to a magnetic field. Hydrogen or proton dipoles in water, blood, and other tissue, and other organic molecules are used most often. Light endowed with OAM will interact with other dipoles, and is not limited to a select few. It is important, however, that the light interacts with the target molecules Infrared light can be used to increase light penetration, for example, to illuminate sub-dermal structures, but at the cost of interaction strength. Also, as previously mentioned, OAM can be imparted to any electromagnetic wave, not just visible light. Using shorter wavelengths would bring the advantage of having greater sub-dermal penetration, but also carrying with it the disadvantage that penetrating radiation is potentially damaging to tissue.

Figure 6:
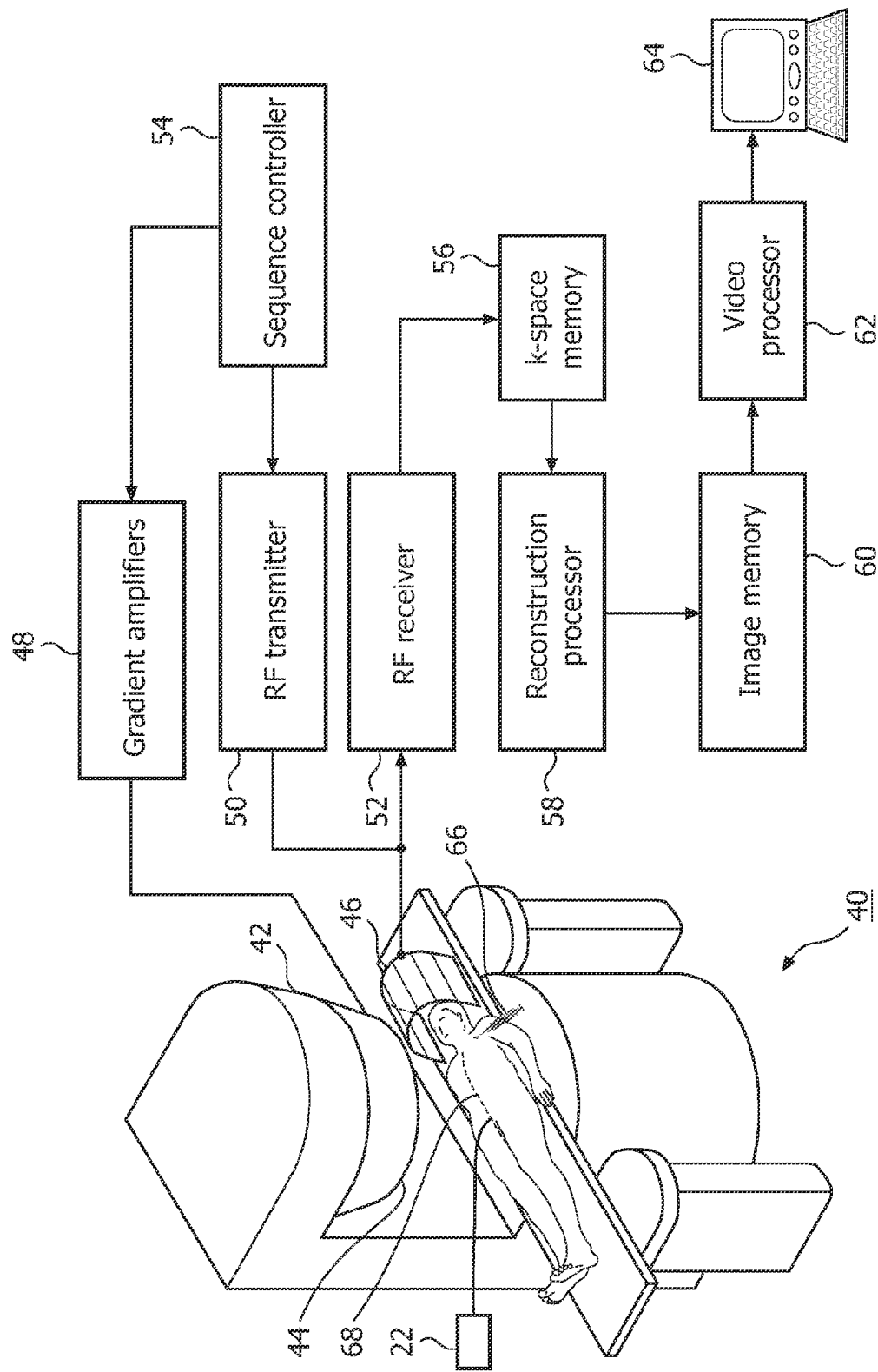
FIG. 6 is a diagrammatic illustration of a magnetic resonance imaging apparatus in accordance with the present application.

In one embodiment, as shown in FIG. 6, the OAM-endowed light-emitting device as described above can be used in conjunction with a magnetic resonance scanner 40. The magnetic resonance scanner 40 can be an open field system (open MRI system) that includes a vertical main magnet assembly 42. The main magnet assembly 42 produces a substantially constant main magnetic field oriented along a vertical axis of an imaging region. Although a vertical main magnet assembly 42 is illustrated, it is to be understood that other magnet arrangements, such as cylindrical, and other configurations are also contemplated.

A gradient coil assembly 44 produces magnetic field gradients in the imaging region for spatially encoding the main magnetic field. Preferably, the magnetic field gradient coil assembly 44 includes coil segments configured to produce magnetic field gradient pulses in three orthogonal directions, typically longitudinal or z, transverse or x, and vertical or y directions. Both the main magnet assembly 42 and the gradient field assembly 44 in some embodiments are used along with optical polarization.

A radio frequency coil assembly 46 (illustrated as a head coil, although surface and whole body coils are also contemplated) generates radio frequency pulses for exciting resonance in dipoles of the subject. The radio frequency coil assembly 46 also serves to detect resonance signals emanating from the imaging region. The radio frequency coil assembly 46 can be used to supplement optical perturbation of previously established polarization.

Gradient pulse amplifiers 48 deliver controlled electrical currents to the magnetic field gradient assembly 44 to produce selected magnetic field gradients. A radio frequency transmitter 50, preferably digital, applies radio frequency pulses or pulse packets to the radio frequency coil assembly 46 to excite selected resonance. A radio frequency receiver 52 is coupled to the coil assembly 46 or separate receive coils to receive and demodulate the induced resonance signals.

To acquire resonance imaging data of a subject, the subject is placed inside the imaging region. A sequence controller 54 communicates with the gradient amplifiers 48 and the radio frequency transmitter 50 to supplement the optical manipulation of the region of interest. The sequence controller 54 may, for example, produce selected repeated echo steady-state, or other resonance sequences, spatially encode such resonances, selectively manipulate or spoil resonances, or otherwise generate selected magnetic resonance signals characteristic of the subject. The generated resonance signals are detected by the RF coil assembly 46, communicated to the radio frequency receiver 52, demodulated and stored in a k-space memory 56. The imaging data is reconstructed by a reconstruction processor 58 to produce one or more image representations that are stored in an image memory 60. In one suitable embodiment, the reconstruction processor 58 performs an inverse Fourier transform reconstruction.

The resultant image representation(s) is processed by a video processor 62 and displayed on a user interface 64 equipped with a human readable display. The interface 64 is preferably a personal computer or workstation. Rather than producing a video image, the image representation can be processed by a printer driver and printed, transmitted over a computer network or the Internet, or the like. Preferably, the user interface 64 also allows a radiologist or other operator to communicate with the sequence controller 54 to select magnetic resonance imaging sequences, modify imaging sequences, execute imaging sequences, and so forth.

In the embodiment illustrated in FIG. 6, a surface probe device 66 that carries the optical device depicted in FIG. 2 is pressed against the carotid artery(s) where it is sufficiently close that the optical light will penetrate to the blood inside. As previously mentioned, the optical device can be used to align or hyperpolarize the nuclei of molecules in the blood flowing past the device. These molecules can then be imaged with the device 40 as they flow through the subject's bloodstream.

In one embodiment, a series of volume images of the brain are generated as the hyperpolarized blood flows into the brain and/or as it washes out. In another embodiment, a single volume image is generated or selected, which illustrates the blood flow in the brain. The images can illustrate penetration of blood into brain tissue, arterial flow, venous flow, etc.

In another embodiment, an inserted catheter or needle probe, as described above, is used to hyperpolarize blood upstream from a region of interest.

Also, as described above, the catheter 68 and the main magnets 42 can work together to align the dipoles of interest, the gradient coil assembly 44 can provide spatial encoding, and the RF coils system 46 can excite and receive resonance.

Figure 7:
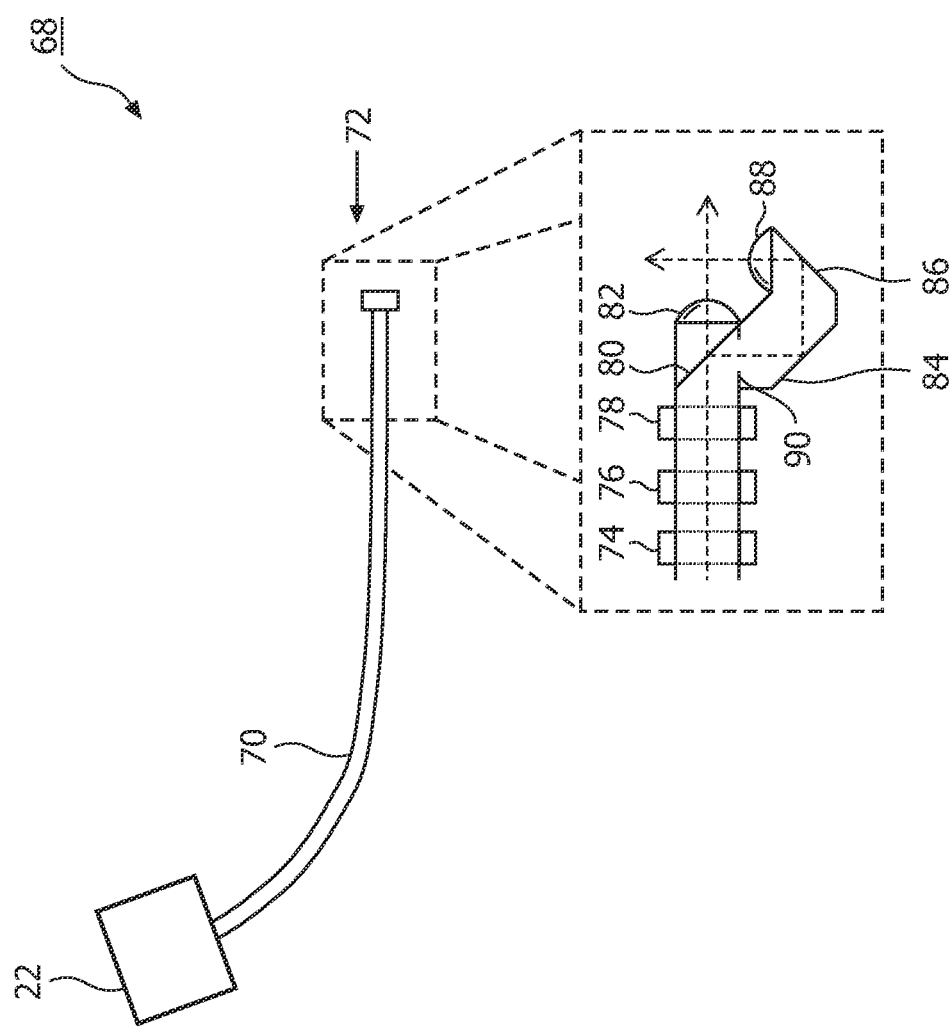
FIG. 7 is a cutaway view of a catheter that carries orbital angular momentum-endowed light, the catheter being capable of being inserted into a patient, in accordance with the present application.

In another embodiment, with reference to FIG. 7, the hyperpolarizing device is contained entirely within the catheter 68 system. The catheter 68 includes an elongated portion 70 and a working end 72 configured for insertion into a patient. The elongated portion 70 includes fiber optics or other light guides to transmit light from the light source 22 to the working end 72. The catheter 68 includes the magnetic elements necessary for magnetic resonance imaging at the working end; the working end includes a magnet 74 for producing a substantially uniform magnetic field at the working end 72 of the catheter, a gradient magnetic coil 76 for encoding the main magnetic field with gradient fields, and an RF coil 78 for exciting and receiving magnetic resonance.

In the illustrated embodiment, polarized light coming through the elongated portion 70 encounters a partially mirrored plate 80 that allows a portion of light to pass to a first objective lens 82. Another portion of light is reflected to a first mirror 84 and on to a second mirror 86 where it then passes through a second objective lens 88, which is oriented orthogonally to the first objective lens. Other optical orientations are certainly possible to arrive at the same result and are also contemplated. A mechanical shutter 90 may be provided so that the orthogonally oriented light may be selectively blocked when it is not desired. Thus, light from the second objective lens 86 can be used to selectively optically manipulate dipoles polarized by light from the first objective lens 82.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The disclosed method can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

Having thus described the preferred embodiments, the invention is now claimed to be:

1. A light-based hyperpolarization device comprising:
 a light source configured to emit light;
 a phase hologram configured to impart orbital angular momentum to the light;
 a spatial filter configured to filter out a portion of the light and to allow a portion of the light with a pre-determined amount of orbital angular momentum to pass; and at least one optical element configured to direct the light that passes the spatial filter to at least one of blood and/or tissue to be hyperpolarized.

2. A magnetic resonance system comprising:
the light-based hyperpolarization device as claimed in claim 1 configured to polarize selected dipoles via transferred orbital angular momentum; and
an RF system configured to induce resonance in the polarized dipoles and configured to receive resonance signals.

3. The magnetic resonance system according to claim 2, further comprising:
a catheter configured to be inserted into a patient, the catheter, comprising a light channel configured to channel light from the light-based hyperpolarization device to a working end of the catheter.

4. The magnetic resonance system according to claim 2, further, comprising:
a gradient magnet system configured to subject the resonating dipoles in an examination region of the magnetic resonance system to a gradient magnetic field.

5. The magnetic resonance system according to claim 2, further comprising:
a gradient magnet system configured to subject the resonating dipoles in an examination region of the magnetic resonance system to a gradient magnetic field, the gradient magnet system being mounted to the catheter adjacent the working end.

6. The magnetic resonance system as set forth in claim 2, wherein the phase hologram is embodied in a spatial light modulator.

7. The magnetic resonance system as set forth in claim 6, wherein the spatial light modulator includes a liquid crystal on silicon panel.

8. The magnetic resonance system as set forth in claim 2, further comprising: a wave polarizer configured to circularly polarize to the light.

9. The magnetic resonance system according to claim 2, wherein the spatial filter blocks a central, undiffracted bright spot of a diffraction pattern, and allows higher order diffraction components carrying orbital angular momentum of a single polarity to pass.

10. A surface probe comprising:
a light output unit configured to direct light to penetrate tissue of a patient; and
the light-based hyperpolarization system as claimed in claim 1 configured to impart orbital angular momentum to generated light, the light to which orbital angular momentum has been imparted being discharged through the light output unit to polarize selected dipoles in the patient.

11. A catheter comprising:
an elongated portion terminating in a working end configured to be inserted in a patient; and
the light-based hyperpolarization system as claimed in claim 1 configured to impart orbital angular momentum to generated light, the light to which orbital angular momentum has been imparted being discharged through the working end to polarize selected dipoles in the patient.

12. The catheter as set forth in claim 11, further comprising a magnet at the working end of the catheter.

13. A magnetic resonance system, comprising:
an RF system configured to induce resonance in dipoles of a region of interest of a subject disposed in an examination region and configured to receive resonance signals from the subject, the light-based hyperpolarization device comprising:
a light source configured to emit light,
a phase hologram configured to impart orbital angular momentum to the light,
a spatial filter configured to filter out a portion of the light and to allow a portion of the light with a pre-determined amount of orbital angular momentum to pass, and
at least one optical element configured to direct the light that passes the spatial filter to a region of interest to be hyperpolarized;
a light-based hyperpolarization device configured to polarize a selected one or more of the dipoles via transferred orbital angular momentum, wherein at least one of: the light based hyperpolarization device is configured to introduce light of a different polarization to phase encode the resonating dipoles, and a gradient magnetic system is configured to apply a gradient magnetic field to phase encode the resonating dipoles.

14. A hyperpolarization device, comprising:
a light source configured to emit light;
a wave polarizer configured to circularly polarize the light;
a phase hologram configured to impart orbital angular momentum to the polarized hot, the phase hologram being embodied in a liquid crystal on silicon panel;
a spatial filter configured to filter out a portion of the light and to allow a portion of the light with a pre-determined amount of orbital angular momentum to pass; and
at least one optical element configured to direct the light that passes the spatial filter to a region of interest to be hyperpolarized, the at least one optical element comprising: a microscope objective lens; and at least one concave mirror configured to focus the light on to the microscope objective lens.

15. A magnetic resonance system comprising:
an RF system configured to induce resonance in dipoles of a region of interest and to receive resonance signals from the region of interest;
a light-based hyperpolarization device configured to polarize at least a selected one of the dipoles of the region of interest via transferred orbital angular momentum, the light-based hyperpolarization device comprising:
a light source configured to emit light,
a phase hologram configured to impart orbital angular momentum to the light,
a spatial filter configured to filter out a portion of the light and to allow a portion of the light with a pre-determined amount of orbital angular momentum to pass, and
at least one optical element configured to direct the light that passes the spatial filter to a region of interest to be hyperpolarized, wherein at least one of: the phase hologram is embodied in a spatial light modulator, a wave polarizer is configured to circularly polarize the light, and the spatial filter blocks a central, undiffracted bright spot of a diffraction pattern, and allows higher order diffractions carrying orbital angular momentum of a single polarity to pass.

16. A method of resonance imaging, the method comprising:
polarizing at least one dipole of at least one blood and/or tissue via transferred orbital angular momentum;
inducing resonance in the at least one polarized blood and/or tissue dipoles; and
receiving resonance signals.

17. The method according to claim 16, further comprising:
phase encoding the induced resonance.

18. The method according to claim 16, further comprising:
prior to polarizing the at least one of blood and/or tissue dipole, disposing the at least one blood and/or tissue dipole in a $B_O$ magnetic field.

19. The method according to claim 16, further comprising: applying magnetic field gradients to the at least one blood and/or tissue dipole.

20. The method according to claim 16, wherein inducing resonance comprises:
applying RF signals to the at least one polarized blood and/or tissue dipole.

* * * * *